(12) United States Patent
Ellis et al.

(10) Patent No.: US 8,322,539 B1
(45) Date of Patent: Dec. 4, 2012

(54) FILTER VIAL

(75) Inventors: Samuel A. Ellis, Oceanside, CA (US);
Kishan G. Hingorani, Oceanside, CA (US)

(73) Assignee: Scientific Plastic Products, Inc., Oceanside, CA (US)

( * ) Notice: Subject to any disclaimer, the term of this patent is extended or adjusted under 35 U.S.C. 154(b) by 0 days.

(21) Appl. No.: 13/411,225

(22) Filed: Mar. 2, 2012

(51) Int. Cl.
*B01D 33/00* (2006.01)

(52) U.S. Cl. .................. 210/416.1; 436/178

(58) Field of Classification Search .......... 210/359, 210/416.1; 436/178
See application file for complete search history.

(56) References Cited

U.S. PATENT DOCUMENTS

| | | | |
|---|---|---|---|
| 3,512,940 A | | 5/1970 | Shapiro |
| 3,832,141 A | | 8/1974 | Haldopoulos |
| 3,955,423 A | | 5/1976 | Ohringer |
| 4,510,058 A | | 4/1985 | Cais et al. |
| 4,734,262 A | | 3/1988 | Bagshawe |
| 4,800,020 A | | 1/1989 | Savas et al. |
| 4,891,134 A | * | 1/1990 | Vcelka .................. 210/359 |
| 4,897,193 A | | 1/1990 | Cais et al. |
| 4,990,253 A | * | 2/1991 | Vcelka .................. 210/359 |
| 5,329,739 A | | 7/1994 | Madl, Jr. |
| 5,549,816 A | | 8/1996 | Harp et al. |
| 5,567,309 A | | 10/1996 | Classon et al. |
| 5,833,860 A | | 11/1998 | Kopaciewicz et al. |
| 5,998,214 A | | 12/1999 | Guirguis |
| 7,138,061 B2 | | 11/2006 | Ellis et al. |
| 7,790,117 B2 | * | 9/2010 | Ellis et al. .................. 422/400 |
| 2010/0300959 A1 | | 12/2010 | Ellis |

FOREIGN PATENT DOCUMENTS

DE 4128923 A1 4/1992

OTHER PUBLICATIONS

International Search Report in Patent Application # PCT/US2009/034736, mailed May 14, 2009.

* cited by examiner

*Primary Examiner* — Fred Prince
(74) *Attorney, Agent, or Firm* — Stetina Brunda Garred & Brucker; Lowell Anderson

(57) ABSTRACT

A filter vial for separating biological and chemical fluids has a cylindrical sidewall with an open top and a closed bottom. A protrusion extends upwards from the middle of the bottom to form an annular recess. A tubular plunger has an open bottom end to which is fastened an annular cup having an outer sidewall sized to fit into and seal against the vial's sidewall. An inner sidewall of the annular cup holds a filter over an opening in the bottom of the plunger and forms a shaped cavity leading to that filter. The annular cup on the plunger fits into the annular recess in the vial to force fluid from the vial through the filter and into the plunger.

55 Claims, 8 Drawing Sheets

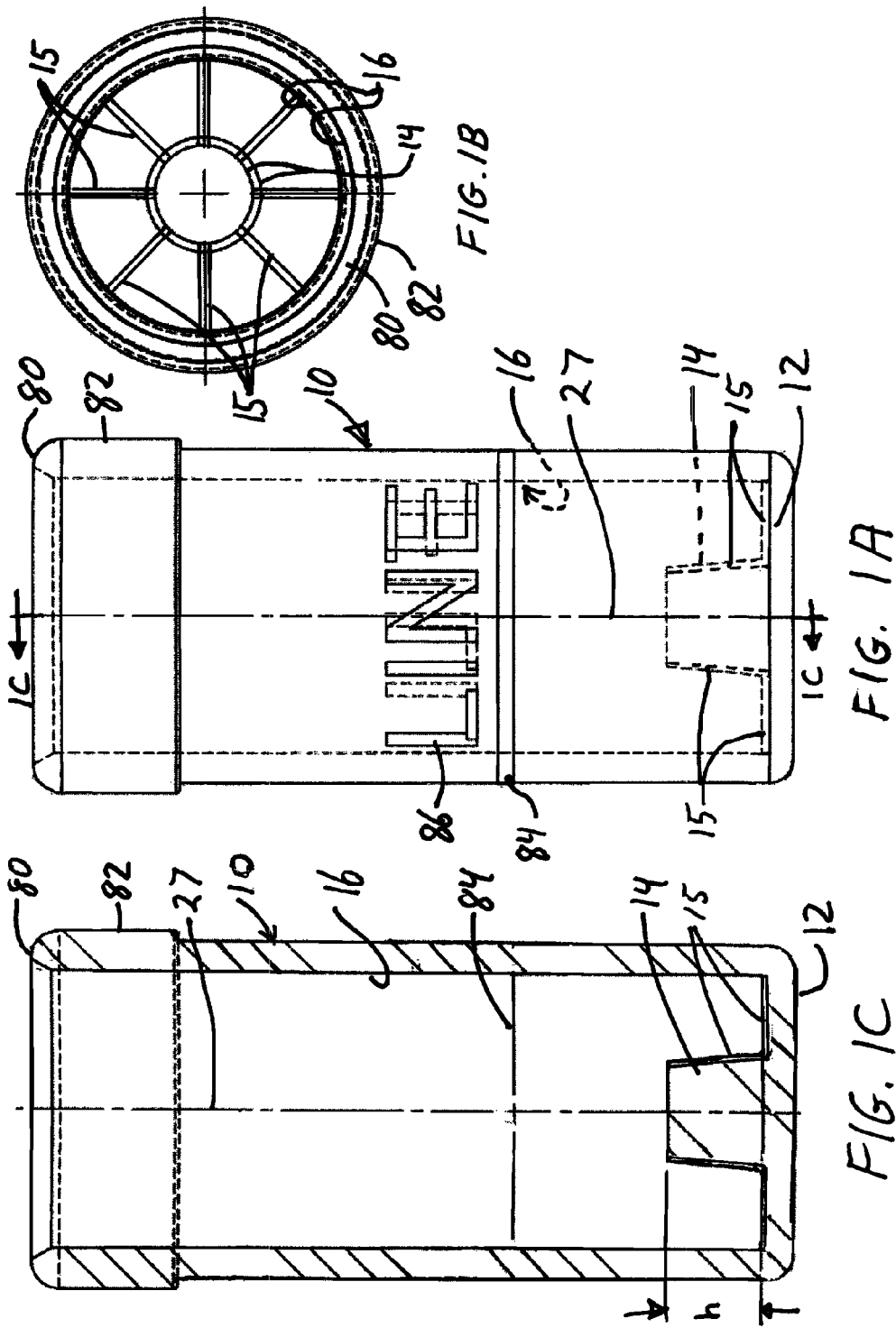

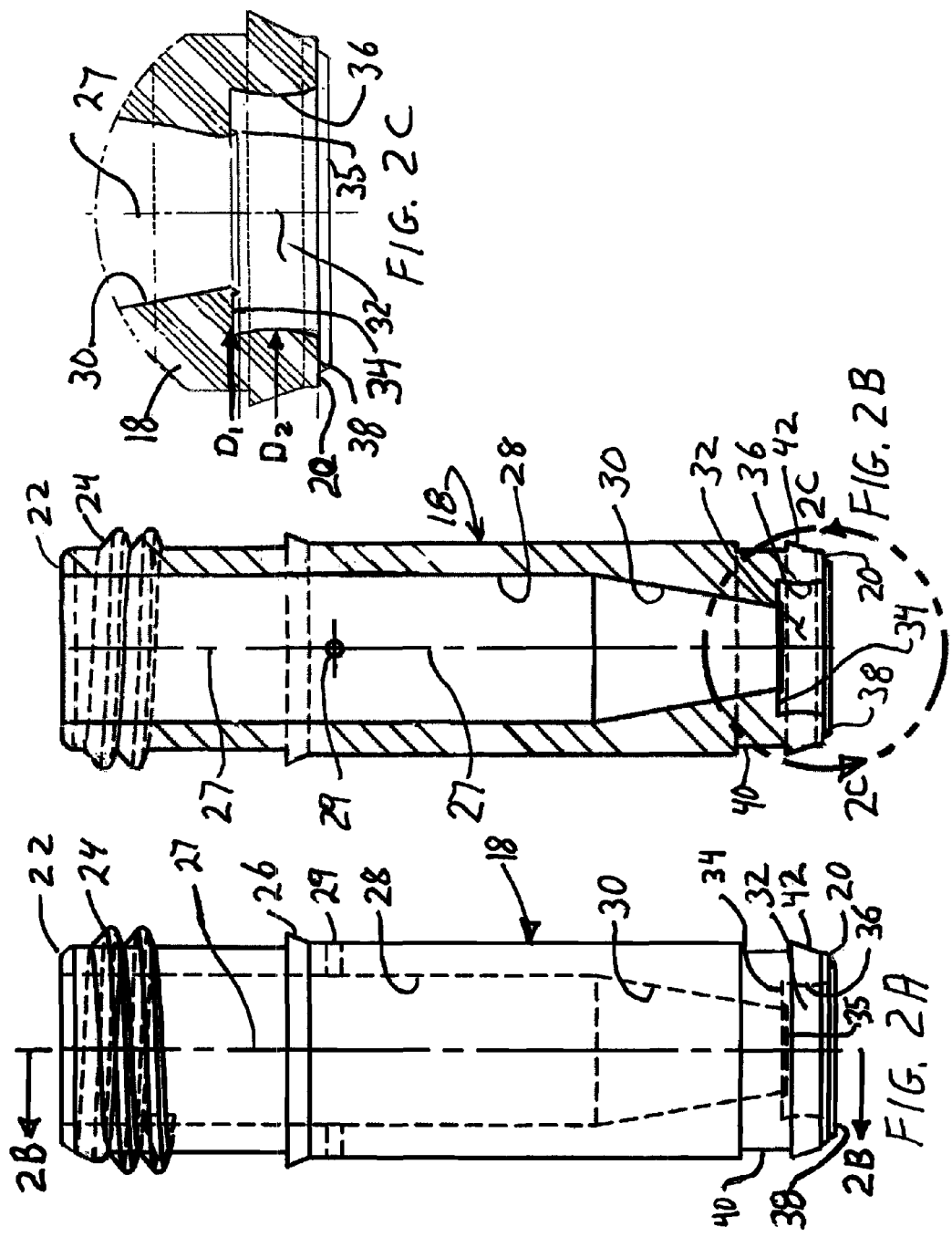

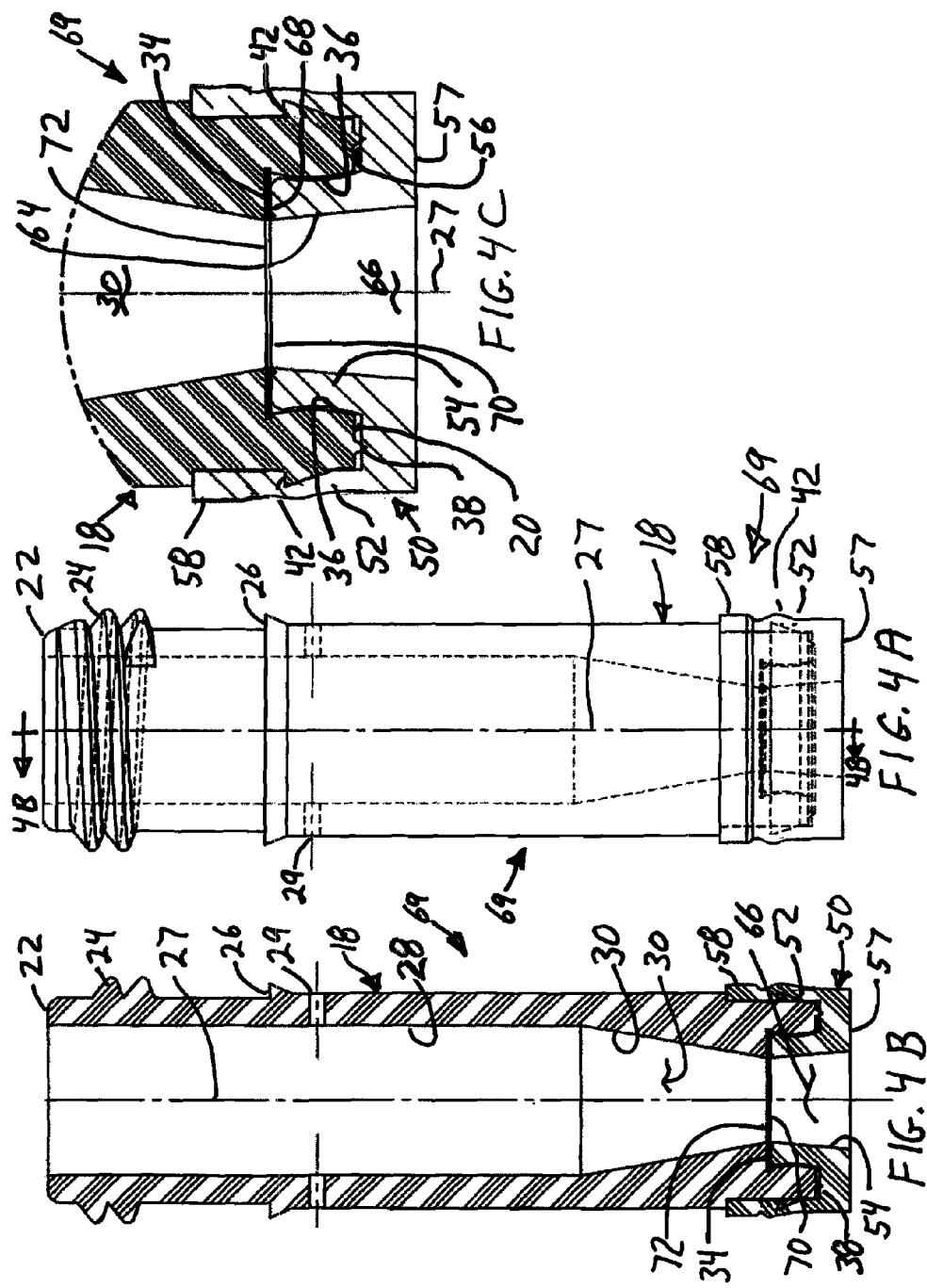

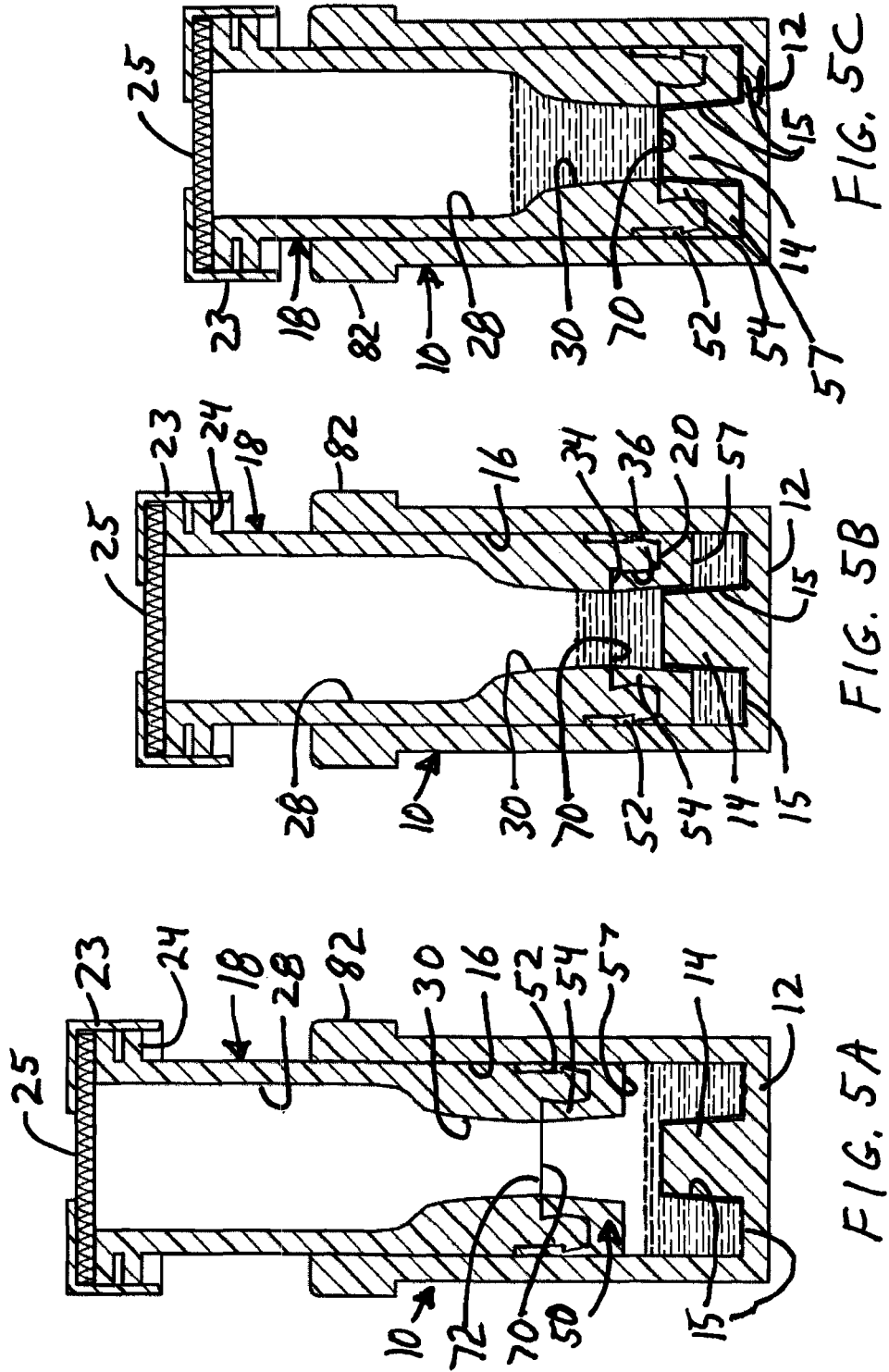

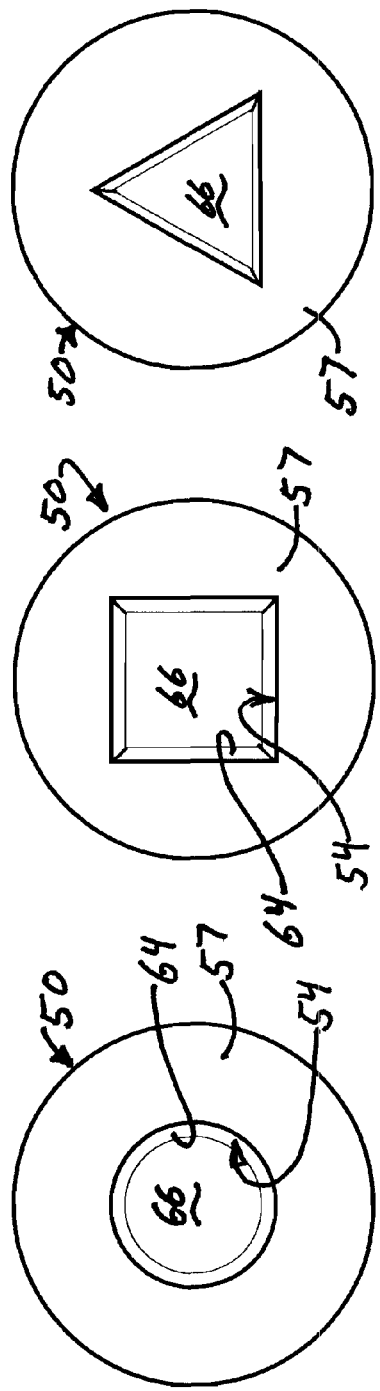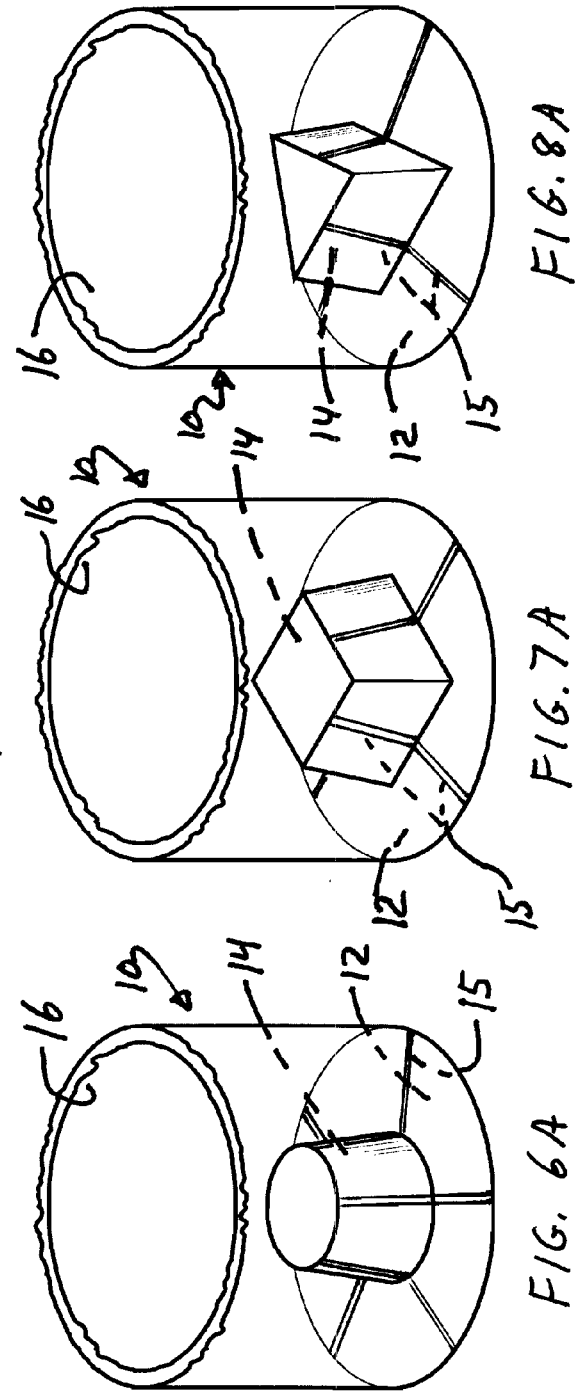

US 8,322,539 B1

FILTER VIAL

CROSS-REFERENCE TO RELATED APPLICATIONS

Not Applicable

BACKGROUND

Filter vials have a tubular plunger with a filter at the bottom end of the plunger. The plunger fits into a mating vial containing a fluid and things suspended in the fluid. When the plunger is inserted into the vial fluid passes through the filter and into the plunger in order to separate the fluid from particles or molecules too large to pass through the filter in the bottom of the plunger. The filtered fluid can be extracted from the plunger for further use.

The diameter and thickness of the filters can vary greatly from filter to filter and the thickness of the filter can vary greatly even across one filter. These variations make it difficult to seal the filters so all the fluid being filtered passes through the filter, and so that fluid does not wick around the peripheral edge of the filter to contaminate the filtered fluid in the plunger. Further, as fluid is forced through the filters the filters can bow or otherwise deform and allow fluid to bypass the filter as it enters the body of the plunger. Many current assemblies use ultrasonically welded assemblies. Even if the filters are ultrasonically welded to the adjacent walls of the assemblies that still leaves plasticizers that may contaminate the fluids placed in the vials during use.

Moreover, current filter vials leave a slight gap between the bottom of the plunger and the bottom of the vial, leaving a portion of the sample unfiltered and unusable for future testing or processing. While the volume of this unfiltered sample may be small in absolute terms, it may represent a sufficiently large portion of the sample that its absence can be important. There is thus a need for a filter vial that avoids the loss of fluid samples and processes more of those samples.

BRIEF SUMMARY

A filter vial for separating biological, chemical or other fluids has a cylindrical sidewall with an open top and a closed bottom. A frustoconical protrusion extends upwards from the middle of the bottom to form an annular recess in the bottom of the vial. A tubular plunger has an open bottom end to which is fastened an annular cup having an outer sidewall that is sized to fit into and seal against the vial's sidewall. The annular cap has an inner sidewall that holds a filter over an opening in the bottom of the plunger and forms a shaped cavity leading to that filter. The space between the cap's inner and outer sidewalls mates with a tubular end of the plunger. The annular cup on the end of the plunger fits snugly into the annular recess in the vial as the protrusion fits into the shaped recess so as to force fluid from the vial past the protrusion, through the filter and into the plunger.

In more detail, there is provided a filter vial and plunger assembly for filtering fluids in which the plunger is a tubular plunger having sidewalls defining an internal fluid cavity. The plunger has a top and bottom ends with a plunger opening in the bottom end of the plunger. An annular cap is connected to the bottom end of the plunger. The annular cap has concentric inner and outer sidewalls with the outer sidewall connected to an outer sidewall of the plunger and the inner sidewall defining a shaped cavity in fluid communication with the plunger opening. The cap's outer sidewall has an outwardly extending first sealing surface at or by its bottom. A filter is interposed between the cap's inner sidewall and the plunger opening to filter fluid passing through the opening. The plunger fits into a vial that has an open top and closed bottom joined by cylindrical sidewalls of sufficient diameter to form a fluid tight seal with the first sealing surface. The vial has a protrusion extending from the center of its bottom toward the top. The annular the bottom of the cap and the bottom of the vial having complementary shapes, including complementary shapes of the protrusion and shaped cavity, to direct fluid from the vial through the shaped cavity during use. Optionally, shallow channels may be formed in the bottom of the vial and in an exterior surface of the protrusion with the channels orientated to carry fluid toward the top of the protrusion. Preferably, but optionally, the protrusion is frustoconical.

There is also provided a filter vial apparatus having a tubular vial with a closed bottom, an open top and a sidewall defining a cylindrical interior with a diameter D located along a longitudinal axis of the vial. The closed bottom has a protrusion extending toward the open top and the vial bottom and protrusion define an annular recess about the vial's longitudinal axis of the vial with the protrusion at the center of the annular recess. The apparatus also includes a tubular plunger assembly having a longitudinal axis. The plunger assembly includes a plunger with opposing top and bottom ends joined by a sidewall to define a fluid holding cavity in the plunger. The plunger's bottom end has an outer annular surface and an inner annular surface axially offset toward the top end from the outer annular surface. The inner annular surface is generally orthogonal to the assembly longitudinal axis and is joined to the first annular surface by a recess sidewall to form a recess that encircles the assembly's longitudinal axis. The second annular surface defines a recess opening that is in fluid communication with the fluid holding cavity of the plunger. The assembly also has an annular cap with inner and outer concentric sidewalls defining an annular recess into which the outer annular surface on the bottom of the plunger is placed. The cap's outer sidewall extends over the outer surface of the bottom of the plunger while the cap's inner sidewall is placed adjacent the sidewall of the recess in the end of the plunger. The inner sidewall of the cap defines a shaped cavity configured to snugly receive the protrusion on the vial's bottom. The shaped cavity has an upper end in fluid communication with the recess opening in the plunger. Further, an outer surface of the outer sidewall of the cap has a diameter sufficiently larger than diameter D to form a fluid tight seal when the plunger assembly is inserted into the vial yet allowing movement of the annular cap to the bottom of the vial. The assembly also includes a filter interposed between the inner annular surface in the plunger and the inner wall of the annular cap. Further, the annular cap on the bottom of the plunger assembly is configured to fit into the annular recess at the bottom of the vial.

In further variations of this filter vial apparatus, the annular cap on the bottom of the plunger conforms in size and shape to the annular recess in the bottom of the vial and forms a snug fit with the bottom and protrusion and a snug fit or a slight interference fit with the vial sidewall. Further, the protrusion and shaped cavity may both be frustoconical with substantially the same dimensions and larger at the bottom than toward the top. Still further, shallow channels may optionally be formed in the bottom of the vial and the sides of the protrusion in order to channel fluid through the channels to the filter. Also, the filter vial assembly may have a releasable end cap on the top end of the plunger, with the end cap configured to provide a fluid seal to the fluid holding cavity of the plunger. Still further, the above filter vial apparatus may optionally have a cap flange on the upper end of the outer sidewall of the cap with the cap flange extending outward from the cap sidewall to provide the outer surface of the outer sidewall of the cap that forms the fluid tight seal with the sidewall of the vial.

The apparatus may also include an outward facing recess in the outer surface of the tubular plunger with that recess located adjacent the bottom end of the plunger and with the cap flange located in that outward facing recess. The plunger may have an outwardly extending plunger flange at or adjacent to the bottom end of the outward facing recess. The outer sidewall of the cap and outward facing recess may be located so the outer sidewall of the cap extends over the plunger flange and into that outward facing recess, with the outer diameter of the outer wall of the cap at the location of the flange having a diameter larger than diameter D to form a fluid tight fit with the sidewall of the vial during use.

The filter vial apparatus may advantageously have the recess sidewall in a convex shape and curved toward the longitudinal axis of the plunger, with the inner sidewall of the annular cap having an outer surface is concave and conforms to the shape of the recess sidewall to nest with the convex surface on the recess sidewall. Further, the vial may advantageously be configured to hold about 10 or fewer micro liters of fluid to be forced through the filter. Advantageously, the bottom of the annular cap may abut the bottom of the vial and less than about 10 micro liters of fluid has passed through the filter into the fluid holding cavity of the plunger. Also, the apparatus may include a frit or filter support on the upper side of the filter and abutting the filter. Preferably, the inner and outer sidewalls of the annular cap each engage a portion of the plunger to hold the annular cap onto the bottom end of the plunger.

In another embodiment, there is provided a filter vial apparatus having a longitudinal axis that includes a vial, a tubular plunger and an annular cap. The vial comprises a cylindrical walled vial with a closed bottom and an open top. The vial has a centrally located protrusion on the bottom that extends toward the top to form an annular recess at the bottom of the vial. The plunger comprises a hollow, tubular plunger that extends into the vial. The plunger has an annular bottom with an axially facing recess therein ending at an annular wall encircling and defining a recess opening in fluid communication with a cavity inside of the tubular plunger. The annular cap has inner and outer sidewalls placed over the annular bottom of the plunger with the outer sidewall on an outer sidewall of the plunger. The outer sidewall has an outer surface a first portion of which extends outward from the longitudinal axis a distance sufficient to form a first sealing surface that forms a fluid tight seal with the cylindrical wall of the vial when the plunger is advanced into the vial a distance sufficient to engage the first portion with the vial's wall during use of the assembly. The inner sidewall of the cap fits into the axially facing recess and extends a distance sufficient to hold a filter against the annular wall of the recess and to also place the filter in fluid communication with the shaped cavity formed by the inner sidewall of the annular cap. The annular cap is configured to fit into the annular recess of the vial with the vial's protrusion snuggly fitting into the shaped cavity.

In further variations of this filter vial assembly, the first sealing surface comprises a flange at the bottom end of the plunger forcing the outer sidewall of the annular cap outward against the vial's sidewall. Preferably, the sealing surface is located at a bottom end of the plunger and annular cap. Further, the assembly may have a second sealing surface on the outer sidewall of the annular cap located upward of the first sealing surface. Advantageously the protrusion is frustoconical in shape and the inner wall of the cap has an inward facing surface that is frusto-conical in shape. Further, the axial facing recess in the end of the plunger may have a sidewall that is convex in shape and the cap may have an outward facing surface on the inner sidewall that is configured to mate with the convex sidewall. Still further, channels in the bottom of the vial may be placed in fluid communication with channels in the surface of the protrusion in order to carry fluid from the container bottom toward the filter during use of the filter vial assembly.

There is also provided a tubular plunger assembly for filtering fluids, for use with various vials. The tubular plunger has at least an open bottom with a fluid holding cavity in the plunger. The plunger has a bottom end with an inner and an outer annular surface which not only encircle and are orthogonal to a longitudinal axis of the plunger but are separated a distance along that by a recess sidewall that encircles and faces the longitudinal axis to define a plunger recess in the bottom end of the plunger. The inner annular surface encircles and defines an opening to the recess which opening is in fluid communication with the fluid holding cavity of the plunger. The plunger assembly has an annular cap with a cap bottom from which extends inner and outer concentric sidewalls configured to fit over the bottom end of the plunger. The outer sidewall fits over an outer surface of the bottom end of the plunger. The inner and outer sidewalls receive the outer annular surface therebetween. The inner sidewall has an outer surface abutting the sidewall of the plunger recess. The inner surface of the inner sidewall defines a shaped cavity in fluid communication with the opening to the recess. The inner sidewall has a top end. A filter is clamped between that top end of the inner sidewall and the inner annular surface.

In further variations, the tubular plunger assembly has a portion of the outer surface of the outer sidewall of the annular cap, at or by the bottom of the annular cap, extending outwardly a distance sufficient to form a first sealing surface that provides a fluid tight seal against a filter vial when the cap is inserted into the vial during use of the plunger assembly. The first sealing surface is advantageously formed by a flange on the end of the plunger which forces a portion of the cap's sidewall outward. The plunger assembly may also include a frit or support interposed between the filter and the first annular surface. Further, the assembly may have a sealing surface facing along and encircling the longitudinal axis and formed on at least one of the first and second annular surfaces. Also, the recess sidewall may have a convexly curved shape in which case the outer surface of the inner sidewall of the cap preferably has a mating concave shape. The shaped cavity is preferably frustoconical in shape. Advantageously, the tubular plunger has a sidewall that is thicker at the location of the second annular surface. Preferably, the plunger assembly may have a removable closure configured to releasably form a fluid tight seal at the top end of the plunger.

There is also provided a filter vial kit that includes any of the above described plunger assemblies as well as a filter vial. The filter vial may have an open top and a closed bottom with a protrusion on the center of the bottom. The protrusion extends toward the top a distance about the same as a height of the inner sidewall of the annular cap measured along the longitudinal axis. The protrusion conforms in shape to the shaped cavity in the cap. The filter vial may also have an internal diameter slightly smaller than the outer diameter of at least a portion of the outer sidewall of the cap on the bottom of the plunger to form the fluid tight seal with the first sealing surface.

In further variations the filter vial kit may include a removable cap and a volume of less than about 30 micro liters. Also, the interior bottom of the vial and protrusion may be configured to conform to the exterior shape of the bottom of the cap and shaped recess. Advantageously, but optionally, the bottom of the filter vial may have shallow channels formed therein which channels are in fluid communication with shallow channels in the surface of the protrusion. The channels are orientated to carry fluid to the top of the protrusion during use.

Another filter vial kit is also provided in which includes a plunger, a filter, an annular cap and a vial. The plunger comprises a hollow tubular plunger having top and bottom ends with an opening at a bottom end of the plunger. The filter extends across the opening in the bottom end of the plunger. The annular cap is fastened to the bottom end of the plunger. An outer sidewall of the cap extends along an outer surface of the bottom end of the plunger with a portion of that outer sidewall extending outward a predetermined diameter to form a first sealing surface. The annular cap has an inner sidewall forming a shaped cavity in fluid communication with the opening in the bottom end of the plunger. The vial has an open top and a closed bottom with the bottom having a central protrusion extending toward the open top of the vial. The vial also has a cylindrical sidewall that is sufficiently smaller in diameter than the predetermined diameter to form a fluid tight seal between the vial and annular cap. The bottom of the annular cap and the shaped recess are configured to mate with the shape of the vial's bottom and the protrusion so as to force fluid in the vial through the shaped cavity and filter.

In further variations of this filter vial kit the bottom of the vial has shallow channels in fluid communication with shallow channels in the surface of the protrusion so fluid is forced through the channels toward the filter as the annular cap fits snuggly against the vial's bottom and its protrusion. Further, the inner sidewall of the cap may push the filter against a portion of the plunger to hold the filter in place. Preferably, the shaped cavity is frustoconical and the protrusion has a mating frustoconical shape with shallow channels in the surface of the protrusion to carry fluid to the top of the protrusion.

An improved filter vial is also provided. The improved vial includes a plastic filter vial having an open top and a closed bottom connected by a cylindrical sidewall. The bottom has a protrusion extending a short distance along a longitudinal axis of the vial toward the top. The filter vial has a volume of about 30 micro liters or less and a sidewall thickness of about 0.050 inches or less. Optionally, the protrusion is frustoconical and extends for a distance of less than about 0.2 inches. Optionally, the bottom of the vial has shallow channels therein that are in fluid communication with shallow channels in an outer surface of the protrusion and orientated to carry fluid through the channels toward the top of the protrusion. The channels are preferably radially orientated.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1A is a side view of a filter vial having a protrusion or boss in its bottom;

FIG. 1B is a top view of the filter vial of FIG. 1A;

FIG. 1C is a cross-sectional view of the filter vial of FIG. 1A taken along 1C-1C of FIG. 1B;

FIG. 2A is a side view of a plunger for use with the filter vial of FIG. 1A;

FIG. 2B is a cross-sectional view of the plunger of FIG. 2A taken along Section 2B-2B of FIG. 2A;

FIG. 2C is an enlarged portion of taken along 2C-2C of FIG. 2B;

FIG. 4A is a side view of the cup of FIG. 3A on the plunger of FIG. 2A;

FIG. 4B is a sectional view taken along section 4B-4B of FIG. 4A;

FIG. 4C is an enlarged sectional view of the lower end of FIG. 4B;

FIG. 5A is a sectional view of the plunger of FIG. 2A with a cup of FIG. 3A inserted into a vial of FIG. 1A, before filtering fluid in the vial;

FIG. 5B is a sectional view of the plunger of FIG. 5A with the plunger forcing some fluid into the plunger;

FIG. 5C is a sectional view of the plunger of FIG. 5A with the plunger abutting the bottom of the vial and all the filtered fluid in the plunger;

FIG. 6A is a partial perspective view of a further embodiment of the vial of FIGS. 1A-1B having a frusto-conical protrusion;

FIG. 6B is a bottom view of a cap having a shaped recess that mates with the annular space and protrusion of FIG. 6A;

FIG. 7A is a partial perspective view of a further embodiment of the vial of FIGS. 1A-1B showing a protrusion with a four sided cross-sectional shape;

FIG. 7B is a bottom view of a cap having a shaped recess that mates with the annular space and protrusion of FIG. 7A;

FIG. 8A is a partial perspective view of a further embodiment of the vial of FIGS. 1A-1B showing a protrusion with a three-sided cross-sectional shape;

FIG. 8B is a bottom view of a cap having a shaped recess that mates with the annular space and protrusion of FIG. 8A;

DETAILED DESCRIPTION

Figure 3C:
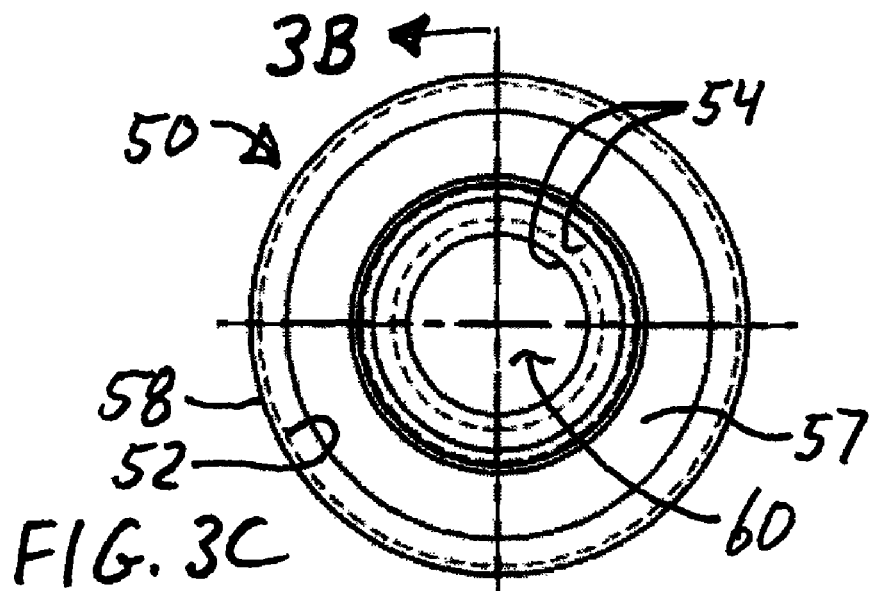
FIG. 3C is a top view of the cup of FIG. 3A.

Briefly described with reference to FIGS. 1A-1C and 5A-5C, a tubular filter vial 10 has a closed bottom 12 with a boss or protrusion 14 located at the middle of the bottom. The protrusion 14 extends into the cavity formed cylindrical wall 16 of the vial forming an annular space between the protrusion 14 and the wall 16 of the vial 10. Shallow channels 15 are formed in the bottom 12 and sides of the protrusion 14. When a fluid sample is placed in the vial 10 the fluid surrounds the protrusion 14. A tubular plunger 18 has a first and outer, annular bottom end 20 over which fits an annular cap 50, with the bottom of annular cap 50 shaped to fill the annular space surrounding projection 14 and fit snugly over the protrusion 14 so as to force all of the fluid in the vial 10 and annular space surrounding projection 14 through a filter 70 in the bottom of the plunger and into the inside of the tubular plunger 18 where the filtered fluid may be removed for further use. The shallow channels 15 in the bottom 12 and sides of projection 14 allow any residual fluid to be forced from the vial through filter 70 and into the plunger 18. The annular bottom end 20 of the plunger 18 is preferably orthogonal to the longitudinal axis 27 of the plunger, but since the end 20 may take various shapes it need not be a flat, annular surface. A removable end cap 23 (FIGS. 5A-5C) on the upper end 22 of the plunger provides a closed container for the filtered fluid. The end cap 23 is removed to access the fluid in the tubular plunger or a needle is inserted through membrane 25 to access the filtered fluid. The end cap 23 may have various configurations and may attach to the end 22 of the plunger 18 various ways, including use of threads 24.

Figure 3B:
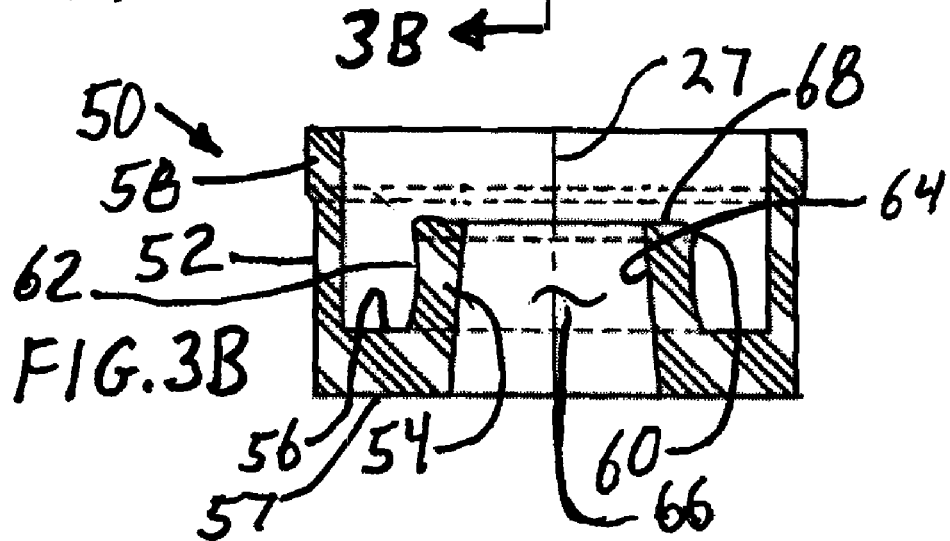
FIG. 3B is a sectional view taken along 3B-3B of FIG. 3C.
Figure 3A:
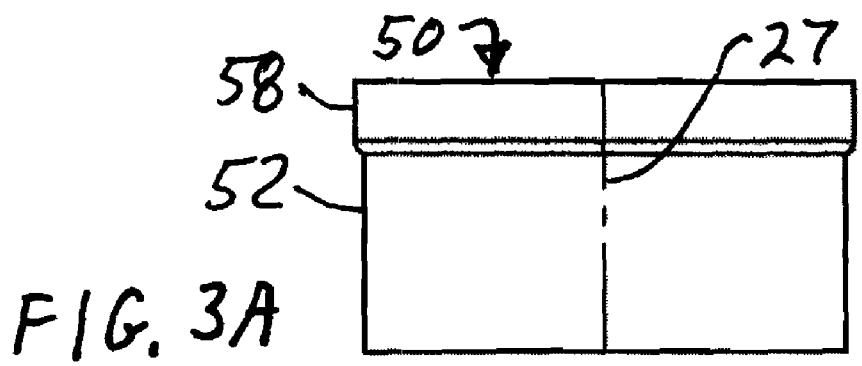
FIG. 3A is a side view of a cup for use with the plunger of FIG. 2A.

The relative directions top and bottom or upper and lower are with respect to the parts as shown in FIGS. 1A, 2A and 3A when the drawings are held vertically. This has the top orientated away from the earth and the bottom toward the earth when the vial and plunger are held vertically in a use position. The relative directions are thus those of a person standing. Similarly, up and down or upper and lower or above and below refer to the relative positions of a person standing with the vial in a vertical orientation. The relative directions inner or inward refer to direction toward common longitudinal axis 27 of the various parts as described later. The relative directions outer or outward refer to the direction away from the common longitudinal axis 27. Further, as used herein, a snug fit means a very close fit that allows parts to fit together when manually positioned but not an interference fit. The space between snugly fitting parts may vary from zero to a few thousandths of an inch (about 0.1 mm or less).

Referring to FIGS. 2A-2C, the tubular plunger 18 has a circular cross-section with bottom and top ends 20, 22, respectively. Threads 24 may be optionally placed on the outer surface of the plunger adjacent the top end 22 with the threads configured to mate with a threaded closure 23 (FIG. 5A) to close off the top end of the plunger, preferably by providing a fluid tight seal. The closure 23 may have an elastomeric membrane 25 through which a needle may be inserted to withdraw portions of the filtered fluid from inside the plunger 18. An upper flange 26 extends outward from the exterior surface of the plunger 18 toward upper end 22 of plunger 18. The upper flange 26 may various cross-sectional shapes, with a triangular cross section being preferred. The triangular cross-section is inclined to make it easy to insert the upper flange 26 into the vial 10 so the flange may seal against the interior wall 16 of the vial while resisting removal of the plunger from the vial. Thus, the flange 26 has one side extending outward from the exterior surface of the plunger 18, and preferably in radial direction from a longitudinal axis 27 of the plunger 18, while another side is inclined so as to intersect the longitudinal axis 27 between the flange 26 and the bottom end 20 of the plunger. A vent hole 29 may be extend through the wall of the plunger 18, with the vent hole advantageously located close to the flange 26, but between the flange 26 and the bottom end 20. The vent hole should be located well above the anticipated fluid level in the plunger 18.

Figure 11:
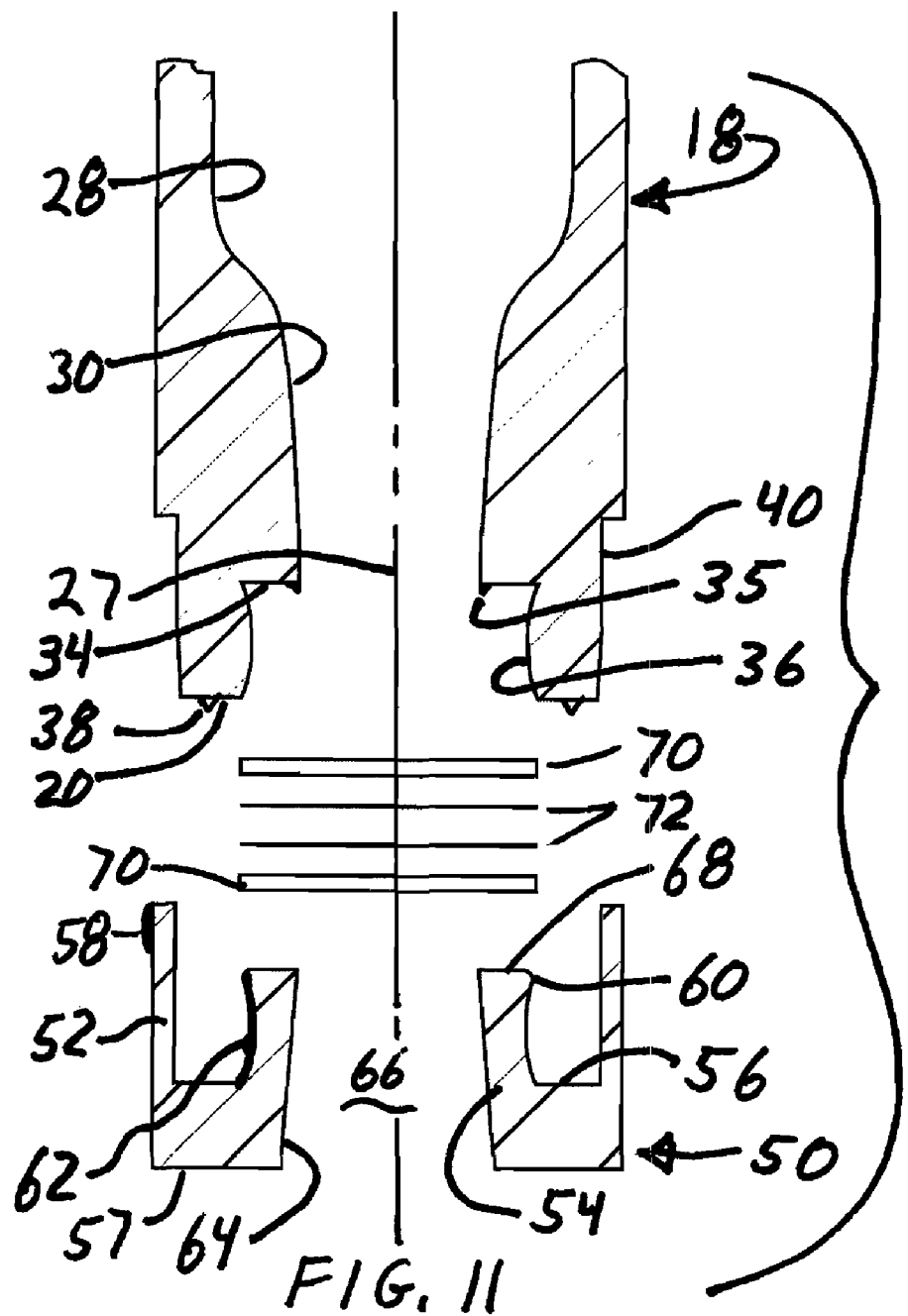
FIG. 11 is an exploded cross-sectional view of a lower portion of a plunger, filters, filter supports or frits, and a cap.

The tubular fluid holding cavity in the plunger 18 preferably has a cylindrical portion 28 beginning at the top end 22 with a narrowing portion 30 beginning about ¼ of the length of the plunger from the bottom end 20. The narrowing portion 30 is optional, but inclined walls forming a truncated, conical surface are preferred. The bottom end of the narrowing portion 30 opens into a larger plunger recess 32 that is formed in the bottom end of the plunger 18. The plunger recess 32 is generally cylindrical in shape, creating a stepped configuration in the bottom portion of the plunger 18. The step may be a sharp change in diameter or a gradual one as shown in FIG. 11. The plunger's annular end 20 encircles the plunger recess 32 and axis 27 so the plunger recess 32 faces along axis 27. The plunger recess 32 extends from the bottom surface 20 toward the top of the plunger for a short distance, ending at annular wall 34, which is generally orthogonal to the longitudinal axis 36 of the plunger and surrounds the lower end of fluid holding cavity 30. The plunger's annular end 20 may be viewed as an outer annular surface generally aligned with or close to the outer periphery of the plunger 18, while the annular wall 34 is an inner annular surface 34 located inward of and laterally offset from the first annular surface 20 toward the upper end 22 of the plunger. Sidewall 36 faces and encircles axis 27 and join the inner edge of the annular surface 20 to the outer edge of annular surface 34. The first and outer annular surface 20 is on the end of a tubular projection formed by the wall of the tubular plunger 16, while the second, inner annular surface 34 is offset therefrom and defines the bottom opening to the fluid holding cavities 28, 30.

The plunger recess 32 has sidewall 36 that may be parallel, inclined, curved or of other shape to help seal with mating parts that may be placed into the plunger recess 32 as described later. A slight curve of the sidewall 36 is believed preferred, with the sidewall being convex so the middle of the sidewall extends more toward the longitudinal axis 27 than the ends of the sidewall 36. Thus, the plunger recess 32 has a maximum diameter of D1 at its top and bottom and a minimum diameter D2 therebetween. As seen in FIGS. 2A-2C, the annular surface or wall 34 is above plunger end 20 so the annular wall 34 may be referred to as top wall 34, of the plunger recess 32. The convex shape of the sidewall 36 helps hold the annular cap 50 on the annular bottom of the plunger 18 as described later.

Advantageously, but optionally, a recess sealing member 35 (FIG. 2C) is formed on the annular top wall 34 and extends along axis 27 in the direction of the bottom of the plunger 18. A seal with a triangular cross section is preferred, and preferably the seal is at the edge of the juncture of the tapered fluid holding cavity 27 and the top wall 34.

An end sealing member 38 is optionally formed on the annular end surface 20. The end sealing member 38 encircles the plunger recess 32 and is centered on axis 27. A end sealing member 38 with a triangular cross-section is preferred, with the seal extending in the direction of the axis 27 away from the plunger's bottom end 20. Advantageously, the end sealing member 38 is formed in about the middle of the annular end surface 20, about half way between the plunger recess 32 and the outer circumference of the plunger's end 20. As seen best in FIG. 2C, the outer surface of the plunger adjoining the end surface 20 may optionally be cylindrical in shape for a short distance upward along axis 27. In contrast, the inner surface of the plunger at the end surface 20 is preferably curved as discussed above.

An annular groove 40 is preferably formed in the outer surface of the plunger 18 adjacent the bottom end 20 and encircling the end of the plunger. The groove 40 may have a flat bottom generally parallel to and concentric with the axis 27 with perpendicular ends. The width of groove 40 extends a short distance along axis 27, with the distance depending at least in part on the configuration of a cap described later. The outer side of the plunger 18 between the lower edge of the groove 40 and the end 20 is generally inclined, forming a plunger flange 42 at the bottom of the plunger. Preferably, the plunger flange 42 is inclined so it intersects axis 27 below the end 20. Further, the largest diameter of plunger flange 42 is preferably the same as that of the cylindrical diameter of the plunger 18. As seen best in FIG. 2C, the plunger flange 42 preferably ends below the plunger recess 32 as measured along the axis 27, with the groove 40 beginning toward the top of the plunger recess 32.

Referring to FIGS. 2B and 2C, the bottom end of the tubular plunger 18 has an outer wall on which is located the plunger flange 42 radially opposite inner wall 36 of the plunger recess 32. As described later, each of these opposing surfaces on the lower end of the plunger 18 seal against a mating surface on the annular cap 50 that may be snapped into place over the lower end of the plunger.

Referring to FIGS. 2-4, the annular cap 50 is dimensioned so that it can be forced over the plunger flange 42 with an interference fit while also mating with the sidewall 36 of the plunger recess 32 to also help hold the cap onto the end of the plunger 18. In use the annular cap 50 is located on longitudinal axis 27. The annular cap 50 has an outer, generally cylindrical and tubular sidewall 52 and an inner generally cylindrical and tubular sidewall 54 joined at the lower ends by bottom 56. The cap's outer sidewall 52 has an outwardly extending flange 58 at its free end. The inner sidewall 54 has an outward extending flange 60 at its free end. The outer sidewall 52 is generally of uniform thickness and is higher than inner wall 54, preferably having the outer wall flange 58 located beyond the end of inner wall 54.

The sidewalls 52, 54 are concentric and spaced apart a distance to receive between them the outer annular surface 20 and the portion of the plunger sidewall on which that annular surface 20 is formed. Advantageously, the cap's sidewalls 52, 54 conform to the shape of the tubular plunger's sidewall on which the annular surface 20 is formed. Thus, the inner and outer sidewalls 52, 54 are concentric, annular walls spaced apart a predetermined distance by bottom 56 on the top side of the cap 50 with a larger bottom 57 of the lower side of the cap 50. The bottom 56 on the upward facing side of the annular cap 50 forms an annular surface extending between the facing portions of the cap's sidewalls 52, 54, and has a radial width extending from the outside of the inner wall 54 to the inside of the outer wall 52. The bottom 57 on the downward facing side of the annular cap 50 forms an annular surface that also extends between the sidewalls 54, 54, but it has a radial width extending from the inside of the inner wall 54 to the outside of the outer wall 52.

The inner sidewall 54 has a curved outer surface 62 (FIG. 3B) with a curvature selected to match the curvature of sidewall 36 of the plunger recess 32 so the sidewalls 54 and 62 nest together. This mating curved shape is believed to not only hold the cap 50 onto the end of the plunger 18 but also helps ensure the inner wall 54 pushes the filter 70 against the inner annular wall 34 to form a fluid tight seal. Thus, in use, the outer surface 62 of the inner annular sidewall 54 abuts the sidewall 36 of plunger recess 32 in the end of the plunger 18, with the sidewalls 54, 36 forming a fluid tight seal.

The inner sidewall 54 has an inner surface 64 (FIG. 3B) shaped to fit over protrusion 14 (FIG. 1C) with a snug fit and optionally with a slight interference fit. Preferably, but optionally, the inner surface 54 is a segment of a conical surface (frustoconical), with the surface tapered to intersect longitudinal axis 27 above the ends of the sidewalls 54, 58. Thus, the cap's inner sidewall 54 forms a shaped cavity 66 centered about longitudinal axis 27. Advantageously, the cap's inner sidewall 54 is inclined outward toward the bottom end of the annular cap 50, and preferably has that outward inclination along the entire length on the inside of the inner sidewall 54. Advantageously, the top 68 (FIG. 3B) of the cap's inner sidewall 54 forms a circular opening that is the same as the circular opening on the inside of inner annular wall 34 of the plunger recess 32 (FIG. 4C), to form an hourglass shape in cross-section, with the filter 70 at the narrow point of the hourglass. The upper end of the inner sidewall 54 forms an annular surface 68 which abuts the filter 70 during use and pushes the filter against the inner annular surface 34 of the plunger 18.

Referring to FIGS. 2-4 and 11 and especially to FIGS. 2C, 3B and 4A-4C the formation of plunger assembly 69 is described in which the cap 50 is placed on the plunger 18 to hold a filter 70 and optionally a frit or support 72 in place. The outer wall 52 has an inner surface with a diameter that is slightly smaller than the largest diameter of the plunger flange 42 of the plunger 18 so that an interference fit is created when the upper end of the annular cap 50 is forced over the lower end of the plunger 18. The cap's outer sidewall 52 is flexible enough so that it bulges slightly outward at the location of the plunger flange 42, with the upper portion of sidewall 52 fitting into groove 40 in the lower end of the plunger. The plunger flange 42 advantageously forms a fluid tight seal with the outer wall 52 of the annular cap 50. During use, the plunger flange 42 is preferably configured so that it has a taper that makes it easier to fit the plunger flange 42 into the cap 50, but hinders removal of the cap from the flange after the parts are engaged.

As the plunger flange 42 seals against the outer wall 52 of the annular cap 50, the outer surface of the inner wall 54 of the annular cap seals against the inward facing surface 36, or sidewall 36, of the plunger recess 32 in the end of the tubular plunger 18. The flange or rib 58 on the outer wall 52 of the cap 50 fits into the groove 40 on the plunger. The flange 58 may abut the upper side of the groove 40 in order to limit relative motion of the outer sidewall 52. The flange 58 within the groove 40 also provides resistance to removing the cap 50 from the plunger.

Likewise, the inner wall 54 both seals against the plunger 18 and hinders removal of the cap from the plunger. In the depicted embodiment the sidewall 36 is convex toward the axis 27 and the outer surface of sidewall 54 is curved (concave) to mate with convex sidewall 36. The cap's inner sidewall 54 engages the plunger sidewall 36 to form a fluid tight seal and help hold the parts together. Other mating shapes could be used on the surface 36 and sidewall 54.

Preferably, the bottom 56 of the annular cap 50 is sized to accept the annular bottom 20 of the plunger 18, with the optional end sealing member 38 abutting the bottom 56 (FIG. 4c). Thus, the annular cap 50 may be forced over the plunger flange 42 on the bottom end of the plunger 18, with the plunger flange 42 forming a snap lock to hold the cap in place, and the cap forming fluid tight seal with the bottom end of the plunger. Further, the annular cap 50 has an outer wall 52 that seals against the outer surface of the plunger 18 at the bottom end of the plunger and advantageously hinders removal of the cap from the plunger. The annular cap 50 further has an inner wall that seals against the inner surface of the plunger 18 (sidewall 36) at the bottom end of the plunger and advantageously also hinders removal of the cap from the plunger. The annular cap 50 defines a fluid passage 66 which the cap 50 places in fluid communication with the opening in the lower end of tapered fluid holding cavity 30.

Advantageously, the cap's inner wall 54 has a height h corresponding to that of protrusion 14 (FIG. 1C) which height also preferably places the upper, annular end 68 (FIG. 3B) of that sidewall 54 immediately adjacent or abutting the top wall 34 of the plunger recess 32 and filter 70 but such that the bottom of the tapered fluid holding cavity 30 (FIG. 4B, 4C) is aligned along axis 27 with the top of shaped cavity 66. Referring to FIGS. 4B-4C, the cap's inner sidewall 54 preferably leaves a slight gap between its upper end 68 and the top wall 34 of plunger recess 32. A filter 70 and preferably but optionally a frit or support 72 are placed in that slight gap. The filter 70 is preferably below the frit or support 72 so that the frit or support 72 can support the filter against upward fluid pressure from shaped cavity 66 into fluid holding cavity 30. The outer periphery of filter 70 and frit or support 72 are clamped between the top wall 34 of the plunger recess 32 (FIG. 2C) and the top end 68 of the inner sidewall 54. There may be any number of filters 70 or frits/supports 72, in various arrangements as partially illustrated in FIG. 11. The number and arrangement of filters 70 and frits or supports 72 will vary with the specific application and design, as will the shape of the filters and frits or supports. In particular, one or more filters 70 may be on the upstream or downstream side of the frit or support 27, and the filters may be separate from or attached to the frit or support 72. Further, because the sidewall 36 of recess 34 is curved, the filter 70 and frit or support 72 may have a diameter large enough to be placed adjacent the larger diameter portion of the sidewall 36 (FIG. 2C) that is immediately adjacent the top wall 34 (FIG. 2C), with the curvature of the sidewall temporarily holding the filter and/or frit or support in place. Moreover, the diameter of the seal 70 and any frit or support 72 are preferably large enough to extend past sealing member 35 on the top wall 34 of cavity 32 in the end of the plunger 18. The sealing member 35 helps provide a fluid tight seal between the top wall 34 and end 68 of the cap's inner wall 54 and any intervening filter or frit/support.

The filter 70 is preferably, but optionally made of Teflon, nylon, glass fiber or other filter materials such as PVDF (polyvinyldifloride) or PES (polyethersulphone), etc. The support or frit 72 is preferably made of the same plastic as the plunger 18 or cap 50, but porous or otherwise allowing fluid passage. Frit 72 may be made of Teflon or glass mesh. Both the filter 70 and fit or support 72 may be very thin when the volume to be passed there through is measured in micro liters. The spacing between the inner sidewall 54 of the cap 50 and top wall 34 of the recess in the plunger 18 are selected to hold these thin parts (filter and/or frit/support) in place without breaking the support 72 and with enough force so fluid may be forced through the filter 70 during use. The inner wall 54 and plunger 18 thus clamp the filter 70 and/or frit or support 70 in position. If the filter is strong enough by itself to safely withstand fluid forced through it during use, the frit/support 72 may be omitted. If not, then a fit or support 72 of suitable thickness and strength is provided. Because the plunger 18 and/or a thicker plunger sidewall may be made of stiffer material than the annular cap 50, or because the shape of the lower end of the plunger 18 makes it much stiffer along the axis 27 at the location of the cap 50, it is believed possible to force the cap 50 and its inner wall 54 sufficiently tight against the plunger 18 so as to clamp the filter 70 between the inner wall 54 and top wall 34 that a support or frit 72 may not be needed for all applications. Thus, the plunger assembly 69 advantageously has both a filter 70 and frit or support 72 interposed between the annular cap 50 and the lower end of the plunger 18, but may omit the fit or support 72.

As reflected in FIG. 4C, when the annular cap 50 is snap-fit onto the bottom end of the tubular plunger 18 to form the plunger assembly 69, the facing portions of curved sidewall 36 and inner sidewall 54 on the sidewall 36 and inner wall are preferably not in an interference fit. Further, the bottom end of the plunger 18 adjacent the bottom end of tapered fluid holding cavity 30 is thicker and thus stiffer than the upper portion of the plunger, thus providing a stiffened plunger end. The tapered fluid holding cavity 30 in the bottom end of the plunger 18 has an opening that is aligned with the opening of shaped cavity 66 in the annular cap 50. The diameter of the tapered fluid holding cavity 30 preferably narrows along the longitudinal axis 27 as you move toward the shaped cavity 66 and the cavity 66 narrows toward the fluid holding cavity 30 along the longitudinal axis as you move toward the fluid holding cavity 30, to form a generally hourglass shape, or to form a venturi shape. As shown in FIGS. 4A and 4B, the resulting plunger assembly 69 has a lower portion of a generally uniform outer diameter except for an outward extending protrusion adjacent the location of flange 58 at the end of cap 50 and/or plunger flange 42.

Referring to FIGS. 1C, 4B, 4C, and 5A, 5B and 5C, the plunger assembly of FIG. 4 is placed into the open end 80 of vial 10. That open end 80 advantageously has an inwardly and downwardly tapered opening to make it easier to align and insert the bottom end of plunger assembly 69 into the vial 10. Advantageously, but optionally, a rib 82 extends around the top end of the vial to provide extra strength around the opening to the vial. The inner diameter of the sidewall 16 of the vial 10 has a diameter corresponding to the diameter of the bottom end of the annular cap 50 or slightly larger. But the inner diameter of the vial's sidewall 16 is smaller than the diameter of the plunger assembly at the location of the cap flange 58, and preferably at the diameter of the plunger flange 42 so as to create an interference fit at both locations when the plunger assembly 69. An interference fit of a few thousandths of an inch (about 0.1 mm or less) at the location of rib 58 and plunger flange 42 within the vial 10 is believed suitable when the volume of fluid being filtered is measured in micro liters, but the amount of interference fit will vary with the materials selected.

Preferably, as the cap's outer sidewall 54 passes over flange 42 (FIG. 2A, 4A) the sidewall 54 bulges slightly outward a distance sufficient to form a primary seal between the annular cup 50 and the sidewall 16 of the vial 10. This primary seal provides a sufficient interference fit so that fluid in the vial 10 does not pass this primary seal. A secondary seal is provided by the interference fit formed by the rib 58 pressing against the inside of the vial's sidewall 16. Advantageously no fluid enters the area between the seals provided by plunger flange 42 and the cap's rib 58 on the outer sidewall 52. Since the fluid in the vial 10 does not pass the fluid seal formed by the plunger flange 42 forcing the cap sidewall 52 outward to abut the inside of the vial's sidewall 16, fluid flows into the plunger 18 as the plunger and vial bottom 12 move toward each other. The inner surface of vial sidewall 16 is preferably slightly tapered to allow the parts to be more easily molded and to increase the slight interference fit between the primary and secondary seals provided by plunger flange 42 and outwardly extending rib 58 on the annular cap 50. A slight taper of a few thousandths of an inch or less (about 0.1 mm or less) over the height of the vial is believed suitable when the vial is about an inch (25 mm) high.

As the plunger assembly 69 moves toward the vial's bottom 12, the shaped cavity 66 in the annular cap 50 on the end of the plunger assembly 69 is aligned with and fits over the protrusion 14 at the vial bottom 12. The protrusion is preferably frusto-conical in shape but other configurations may be used as shown in FIGS. 6-10 and discussed later. More importantly, the shape of the protrusion 14 is shaped to fit snugly into the shaped cavity 66. As the plunger assembly 69 is advanced along axis 27 toward the vial's bottom vial 12, the seal between the plunger assembly 69 and the vial sidewall 16 forces fluid toward the vial bottom 12, through the shaped cavity 66 and the filter 70 and into the body of the plunger 18 represented by cavies 30, 28.

Referring further to FIG. 5B and FIG. 1C, as the bottom end of the plunger assembly 69 reaches and passes the top of the protrusion 14, the remaining fluid in the vial 10 is forced between the inclined sides of the protrusion 14 and the mating sides of shaped cavity 66 to force the fluid through the filter 70 and into the fluid holding cavity 30 and/or 28. Referring further to FIG. 5C and FIG. 1C, when the bottom end of plunger assembly 69 abuts the bottom 12 of the vial 10, almost all or all of the fluid along the vial's bottom 12 and protrusion 14 is forced through the filter 70 and the top of the protrusion 14 preferably abuts the filter 70, and ideally may slightly push against the filter 70 but not break the filter and any frit or support 72. The channels 15 in the vial's bottom 12 and sides of protrusion 14 form fluid passageways to allow fluid in the vial to pass through filter 70. As the cap's outer sidewall 52 seals against the vial sidewall 16 fluid is forced toward vial bottom 12 and as the cap's bottom 57 is pushed against the vial's bottom 12 any trapped fluid is forced into the shallow channels 15 and forced through filter 70. Indeed, if the plunger assembly 69 is forced against the vial bottom 12, the bottom 57 of annular cap 50 may be forced slightly into the shallow channels 15 and provide sufficient pressure to move any trapped fluid through the channels 15 and through the filter 70 as the top of the protrusion 14 abuts the filter. Channels a few thousandths of an inch or less deep (about 0.1 mm or less) and about the same in width are believed suitable. Four to eight channels are believed suitable but the number and size of the channels 15 will vary with the particular design and size of the vial 10.

Figure 9B:
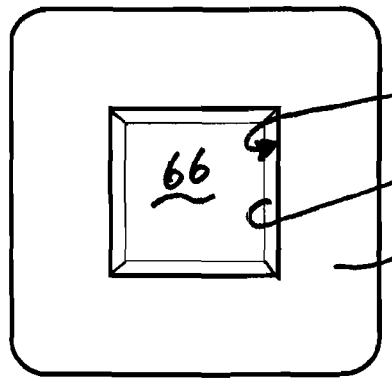
FIG. 9B is a bottom view of a cap having a shaped recess that mates with the annular space and protrusion of FIG. 9A.
Figure 10B:
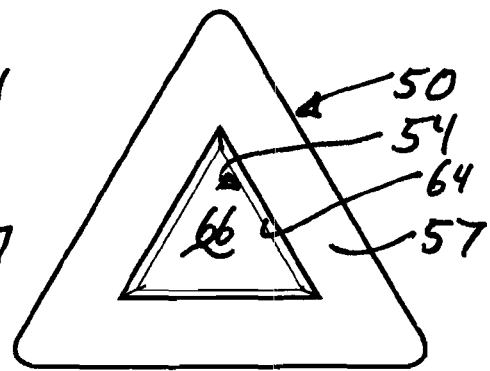
FIG. 10B is a bottom view of a cap having a shaped recess that mates with the annular space and protrusion of FIG. 10A.
Figure 9A:
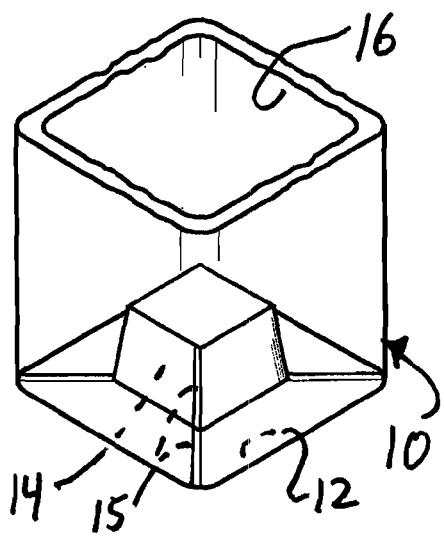
FIG. 9A is a partial perspective view of a further embodiment of the vial of FIGS. 1A-1B showing a protrusion with a four sided cross-sectional shape in a vial with a four sided cross-sectional shape.
Figure 10A:
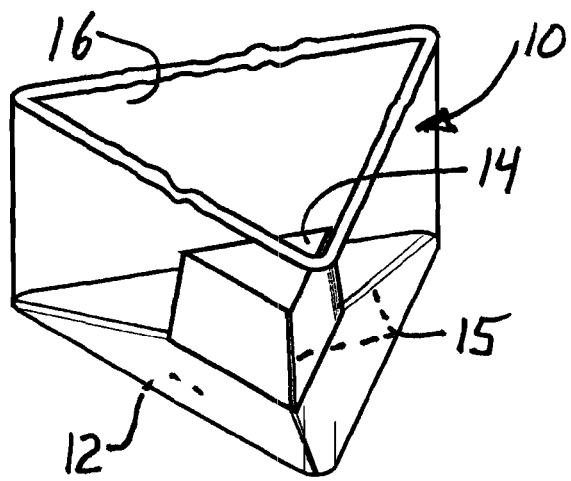
FIG. 10A is a partial perspective view of a further embodiment of the vial of FIGS. 1A-1B showing a protrusion with a three-sided cross-sectional shape.

The cap 50 on the bottom end of plunger 18 thus forms an annular male protrusion formed by the outer surface of the cap's outer sidewalls 52 and the inner surface of the cap's inner sidewall 54, with the shaped recess 66 at the center of the male protrusion. The annular male protrusion is effectively formed by the bottom 57 and sidewalls 52, 54 of the cap 50 that is fastened to the bottom end of the plunger 18. A complimentary shaped annular, female recess is formed by the vial's sidewall 16, bottom 12 and protrusion 14. Likewise the male protrusion 14 in the vial is shaped to mate with the female recess of the shaped cavity 66. The male protrusions and female recesses fit together to squeeze any fluid between them toward the center protrusion 14 and into the body of the tubular plunger and fluid holding cavity 30 and/or 28. The mating annular shapes of the end of the plunger (provided by the shape of the bottom portion of the annular cap) on the one hand and the annular recess of the vial on the other hand, provide means for minimizing the dead volume at the bottom of the vial, with the shaped protrusion 14 and correspondingly shaped recess 66 directing the fluid through filter 70 and into the body of plunger 18 and with the channels 15 in the vial bottom 12 and sides of the protrusion 14 allowing any small trapped portions of the fluid to be forced through the channels and through filter 70 abutting protrusion 14. While the annular space is circular in the depicted embodiment of FIGS. 1-5, the annular space need not be cylindrically based as the mating shape of the protrusion 14 and recess 66 may be non-circular, and the shape of the vial's sidewall 16 and plunger 18 need not be cylindrical but may be any tubular shape, including shapes with continuous curves such as circular or oval, or shapes with straight sides including triangular, quadrilateral or multilateral. Thus, as used herein the use of "annular" is not limited to shapes or volumes having concentric circles, but includes shapes other than circles. For example, FIGS. 7-8 show a protrusion 14 with a cross-section shape of a triangle and quadrilateral, respectively, but in a cylindrical vial 10, while FIGS. 9-10 show protrusions with three and four sides, respectively, in vials 10 having the same number of sides. The space surrounding the protrusion 14 and enclosed by the vial sidewall 16 is still "annular" as used herein. As used herein, the space is annular when the vial sidewall 16 is non-circular in cross section as in FIGS. 9-10, and had, for example cross-sectional shapes that were continuous curves such as circles or ovals, or shapes having straight sides including three, four or more sides joined by corners that were preferably, but optionally rounded. As seen in FIGS. 7-10, the shaped cavity 66 in cap 50 conforms to the shape of the protrusion to form a snug fit. In multi-sided configurations of the protrusion 14 the corners are preferably rounded but may be sharp as shown, with the corners of the shaped cavity 66 preferably conforming to the corners of the protrusion to form a snug fit.

Further, the outwardly inclined surfaces of the vial's male protrusion 14 and of the cap's inner sidewall 54 cooperate with plunger 18 to provide means for deforming the outer sidewall 52 and bottom 57 of the cap 50 against the vial's sidewall 16 and bottom 12, respectively, to reduce the fluid retained between the plunger assembly 69 and vial's sidewall 16 and bottom 12 as the plunger is moved against the bottom 12 of the vial. The primary seal between the vial's sidewall and the plunger flange 42 and bulging cap sidewall 52 is an interference fit which forces fluid in the vial 10 downward toward the vial bottom 12 as the plunger 18 moves the primary seal toward the vial's bottom 12 where the trapped fluid is directed by the mating surfaces of annular cap 50, channels 15 and protrusion 14 to pass through the filter 70. As the bottom 57 and inner sidewall 54 of the annular cap 50 approach a snugly fit against the vial's bottom 12 and protrusion 14, any remaining fluid is forced through channels 15, through filter 70 and into the plunger cavity or cavities 28, 20.

While preferred, it is not believed necessary for both the protrusion 14 and inner sidewall 54 to both have lower portions inclined outward from axis 27. But is preferred as it is believed that the outward inclination of the protrusion 14 mating sidewall 54 of the annular cap 50 help deform the cap's outer sidewall 52 outward against the vial's sidewall 16 and toward the vial's corner where the vial's sidewall 16 joins bottom 12 so as to squeeze any remaining fluid into and through the shallow channels 15 through the filter 17.

The downward movement of the plunger 18 and cap 50 are limited by the cap bottom 57 abutting the vial bottom 12. At about the time the bottom 57 of the cap on the plunger assembly 69 reaches the top of the protrusion 14, or shortly before, the upper flange 26 on the plunger abuts the wall 16 and advantageously forms a further fluid tight seal. The upper flange 26 is located on the plunger 18 to engage the sidewall 16 when the cap's bottom 57 on the plunger assembly 69 is adjacent the top of protrusion 14. Likewise, the diameter of flange 26 is selected relative to the diameter of the wall 16 to form a suitable seal. The engagement of upper flange with the vial sidewall 16 helps stabilize the plunger 18 as it is pushed into the vial, and helps align the bottom of cap 57 with the vial bottom 12. An optional fill line 84 may be provided on the outer surface of the filter vial 10 to indicate a preferred fluid level for use with the vial. As desired, printed indicia 86, such as "fill line" may also be provided adjacent the fill line 84 to more clearly identify the purpose of the line.

There is thus advantageously provided an annular cap 50 with inner and outer sidewalls 54, 52, respectively. The inner sidewall is preferably outwardly inclined or curved at the bottom of the sidewall. The annular cap 50 is preferably molded of an elastomeric material, and preferably one that is incompressible. The annular cap 50 and inclined sides cooperate with protrusion 14 having an outwardly inclined wall at the bottom 12 of the vial 10, so as to force the outer wall 52 of the annular cap 50 toward the vial's sidewall 16 in order to force fluid away from the sidewall and toward the bottom 12 of the vial where it is forced upward past the cap's inner sidewall 54, through the through filter 17 and into cavities 30 and/or 28 in the tubular plunger 18.

The plunger 18, annular cap 50 and vial 10 are preferably molded of a suitable plastic, preferably one that does not contaminate samples placed in the vial 10. The fluid samples are commonly chemical or biological samples, but any fluid to be separated may be used. The vial and annular cap are preferably made of polyolefin, preferably polypropylene, or other suitable polymer that does not react with the intended fluid to be separated using the vial 10. The plunger 18 is advantageously made of a stiffer material, or thicker material than the cap 50 so it is sufficiently stiff to allow plunger 18 to be forced into the cap 50 and to further deform the cap 50 into and against the vial's bottom 12 and protrusion 14. That stiffness may be achieved by using a different material, or by configuring the plunger 18 to be stiffer, as by a thicker sidewall at the location during use of the sealing surfaces formed by flange 40 and rib 58.

There is also advantageously provided a method for filtering fluid samples using a filter vial. The annular cap 50 is fit onto the end of the tubular plunger 18, with the cap's inner wall 54 placing the cavity defined by that inner wall in fluid communication with the internal fluid holding cavity 28, 30 of the tubular plunger 18, and with the cap's inner wall also clamping the filter 70 against the top wall 34 of the plunger recess 32 in the end of the plunger 18. Advantageously the step of placing the annular cap 50 on the end of the plunger 18 also includes snap-fitting the cap over a barb or plunger flange 42 on the plunger to releasably fasten the cap to the plunger. The cap 50 forms an annular shaped protrusion on the end of the plunger holding the filter covering the shaped cavity 66 formed by the inner sidewall 54 of the annular cap. Fluid is placed in vial 10, preferably up to the level indicated by fill line 84, before or after the cap is placed on the plunger. The bottom of the plunger and cap are then inserted into the opening 80 of the vial and pushed toward the vial bottom 12 (or vice versa), with the bulge in outer cap wall 52 formed by plunger flange 42 and/or the flange 58 on the cap 50 forming a fluid tight seal with the vial wall 16. Further relative movement of the plunger assembly 69 toward the vial bottom 12 forces fluid through the shaped cavity 66 in the annular cap 50, through filter 70 and into one or both internal cavities 28, 30 of the plunger. As the bottom end 57 of the plunger assembly 69 passes the protrusion 14, the annular end of the plunger assembly enters the annular bottom of the vial 10, with the mating shapes forcing fluid upward, past central protrusion 14, through the shaped cavity 66 and filter 70 and into the cavities 28 and/or 30 in the body of the tubular plunger 18. The process may include placing a cap on the upper end of the tubular plunger 18, preferably before affixing the annular cap to the bottom end of the plunger, and preferably before forcing fluid into either fluid holding cavity 28, 30 inside the plunger 18.

The above apparatus and process are believed to force much more of the fluid sample through the filter 70 than prior filter vials. When small fluid samples are used the improvement in the volume filtered is especially noticeable. The filter vial 10 is believed especially suitable for fluid samples of about 10 μl, but may be used with larger samples where maximum sample recovery is important. Thus, the fill line 84 is preferably located to contain about 10 micro liters between the fill line and the bottom 12. The method and apparatus are even more useful when the fluid samples are smaller than 10 μl, such as samples of 1 through ten micro liters in one micro-liter increments. While the working volume of the vial 10 is preferably about 10 micro liters or smaller, the total volume of the vial may be about 30 micro liters or slightly larger. A vial 10 having an internal diameter of about one third inch (8 mm) in diameter and about one inch (25 mm) long with walls about 40 thousandths of an inch (1 mm) thick is believed suitable. While the plunger and vial are especially suited for small fluid samples, the design is applicable to larger parts. The cost of the fluid filtered by the vial, plunger, annular cap and filter can be significant, and even small volumes of fluid may be important and costly. Thus, this disclosure is not limited to fluid samples measured in a few micro liters but may include much larger samples of milliliter volumes and even larger.

The plunger 18 is preferably made of an equally strong or stronger and harder material than the annular cap 50. The thickened end of the plunger 18 formed by the tapered internal fluid holding cavity 30 allows a stronger end. But the fluid holding cavity 30 need not be tapered and could be the same diameter as fluid holding cavity 28 in the upper portion of the plunger. The fluid holding cavity 30 could also have a stepped interior shape with one or more steps that reduce the diameter of the cavity 28 as it approaches end 20. Regardless of the shape of the cavity 28, it is preferred that the cavity result in thickened wall of the plunger 18 at the groove 40 and flange 58 which at least partially fits into that groove. A thickened plunger wall provides a strong support to urge the seals formed by flanges 58, 42 into sealing contact with the cap 50 and sidewall 16 of vial 10. Preferably the plunger 16 is of the same material as the annular cap 50, but the cap's outer sidewall 52 is made thin enough to flexibly extend over plunger flange 42 and into groove 40.

The above description is given by way of example, and not limitation. Given the above disclosure, one skilled in the art could devise variations that are within the scope and spirit of the invention disclosed herein, including various ways of shaping the flanges 45, 58 and protrusion 14 and shaped cavity 66. For example, as shown in FIGS. 7-8, the protrusion 14 and shaped cavity 66 may have various mating configurations other than the preferred frusto-conical shape shown in FIGS. 1, 5 and 6, including, but not limited to oval shapes and multisided configurations. FIGS. 7-8 show protrusions 14 and correspondingly shaped cavities 66 having three sides and four sides respectively. If flat sided protrusions 14 are used the corners of the protrusion and mating cavity 66 in the cap are preferably, but optionally rounded as the curved corners are believed to make the parts easier to make. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A filter vial apparatus, comprising:
  a tubular vial having a closed bottom, an open top and a sidewall defining a cylindrical interior with a diameter D located along a longitudinal axis of the vial, the closed bottom having a protrusion extending toward the open top, the vial bottom and protrusion defining an annular recess about the vial's longitudinal axis of the vial with the protrusion at the center of the annular recess;
  a tubular plunger assembly having a longitudinal axis, including:
    a plunger with opposing top and bottom ends joined by a sidewall to define an fluid holding cavity in the plunger, the bottom end having an outer annular surface and an inner annular surface axially offset toward the top end from the outer annular surface, the inner annular surface generally orthogonal to the assembly longitudinal axis and joined to the first annular surface by a recess sidewall to form a recess that encircles the assembly's longitudinal axis, the second annular surface defining a recess opening that is in fluid communication with the fluid holding cavity of the plunger;

an annular cap having inner and outer concentric sidewalls defining an annular recess into which the outer annular surface on the bottom of the plunger is placed, the cap's outer sidewall extending over the outer surface of the bottom of the plunger and the cap's inner sidewall being placed adjacent the sidewall of the recess in the end of the plunger, the inner sidewall of the cap defining a shaped cavity configured to snugly receive the protrusion on the vial's bottom, the shaped cavity having an upper end in fluid communication with the recess opening, an outer surface of the outer sidewall of the cap having a diameter sufficiently larger than diameter D to form a fluid tight seal when the plunger assembly is inserted into the vial yet allow movement of the annular cap to the bottom of the vial;

a filter interposed between the inner annular surface in the plunger and the inner wall of the annular cap;

wherein the annular cap on the bottom of the plunger assembly is configured to fit into the annular recess at the bottom of the vial.

2. The filter vial apparatus of claim 1, wherein the annular cap on the bottom of the plunger conforms in size and shape to the annular recess in the bottom of the vial and forms a snug fit with the bottom and protrusion and a snug fit or a slight interference fit with the vial sidewall.

3. The filter vial apparatus of claim 1, wherein the protrusion and shaped cavity are both frustoconical with substantially the same dimensions and larger at the bottom than toward the top.

4. The filter vial apparatus of claim 1, wherein shallow channels are formed in the bottom of the vial and the sides of the protrusion to channel fluid through the channels to the filter.

5. The filter vial apparatus of claim 1, further comprising a releasable end cap configured to provide a fluid seal to the fluid holding cavity of the plunger at the top end of the plunger.

6. The filter vial apparatus of claim 1, wherein the upper end of the outer sidewall of the cap has a cap flange extending outward therefrom to provide the outer surface of the outer sidewall of the cap that forms the fluid tight seal with the sidewall of the vial.

7. The filter vial apparatus of claim 6, further comprising an outward facing recess in the outer surface of the tubular plunger and located adjacent the bottom end of the plunger with the cap flange located in that outward facing recess, the plunger further having an outwardly extending plunger flange at or adjacent to the bottom end of the outward facing recess, the outer sidewall of the cap and outward facing recess being located so the outer sidewall of the cap extends over the plunger flange and into that outward facing recess, with the outer diameter of the outer wall of the cap at the location of the flange having a diameter larger than diameter D to form a fluid tight fit with the sidewall of the vial during use.

8. The filter vial apparatus of claim 1, wherein the recess sidewall is convex and curved toward the longitudinal axis of the plunger and wherein the inner sidewall of the annular cap has an outer surface is concave and conforms to the shape of the recess sidewall to nest with the convex surface on the recess sidewall.

9. The filter vial apparatus of claim 1, wherein the vial is configured to hold about 10 or fewer micro liters of fluid to be forced through the filter.

10. The filter vial apparatus of claim 1, further comprising a frit or filter support on the upper side of the filter and a abutting the filter.

11. The filter vial apparatus of claim 1, wherein the plunger assembly is in the vial and fluid that has passed through the filter is in the fluid holding cavity of the plunger.

12. The filter vial apparatus of claim 11, wherein the bottom of the annular cap abuts the bottom of the vial and less than about 10 micro liters of fluid has passed through the filter into the fluid holding cavity of the plunger.

13. The filter vial apparatus of claim 1, wherein the inner and outer sidewalls of the annular cap each engage a portion of the plunger to hold the annular cap onto the bottom end of the plunger.

14. The filter vial of claim 1 wherein the diameter D extends over a majority of the length of the vial from the closed bottom of the vial toward the top of the vial.

15. A filter vial apparatus having a longitudinal axis, comprising:

a cylindrical walled vial with a closed bottom and an open top, the vial having a centrally located protrusion on the bottom that extends toward the top to form an annular recess at the bottom of the vial;

a hollow, tubular plunger extending into the vial, the plunger having an annular bottom with an axially facing recess therein ending at an annular wall encircling and defining a recess opening in fluid communication with a cavity inside of the tubular plunger;

an annular cap having inner and outer sidewalls placed over the annular bottom of the plunger with the outer sidewall on an outer sidewall of the plunger, the outer sidewall has an outer surface a first portion of which extends outward from the longitudinal axis a distance sufficient to form a first sealing surface that forms a fluid tight seal with the cylindrical wall of the vial when the plunger is advanced into the vial a distance sufficient to engage the first portion with the vial's wall during use of the assembly, the inner sidewall of the cap fitting into the axially facing recess and extending a distance sufficient to hold a filter against the annular wall of the recess and to place the filter in fluid communication with the shaped cavity formed by the inner sidewall of the annular cap, the annular cap being configured to fit into the annular recess of the vial with the vial's protrusion snuggly fitting into the shaped cavity.

16. The filter vial assembly of claim 15, wherein the first sealing surface comprises a flange at the bottom end of the plunger forcing the outer sidewall of the annular cap outward against the vial's sidewall.

17. The filter vial assembly of claim 15, wherein the first sealing surface is located at a bottom end of the plunger and annular cap.

18. The filter vial assembly of claim 17, further comprising a second sealing surface on the outer sidewall of the annular cap located upward of the first sealing surface.

19. The filter vial assembly of claim 15, wherein the protrusion is frusto-conical in shape and the inner wall of the cap has an inward facing surface that is frusto-conical in shape.

20. The filter vial assembly of claim 19, wherein the axial facing recess in the end of the plunger has a sidewall that is convex in shape and the cap has an outward facing surface on the inner sidewall that is configured to mate with the convex sidewall.

21. The filter vial assembly of claim 15, wherein channels in the bottom of the vial are in fluid communication with channels in the surface of the protrusion to carry fluid from the container bottom toward the filter during use of the filter vial assembly.

22. The filter vial apparatus of claim 15 wherein the vial has a constant inner diameter extending over a majority of a length of the vial from the closed bottom of the vial toward the top of the vial.

23. A tubular plunger assembly for filtering fluids, comprising:
a tubular plunger having at least an open bottom with a fluid holding cavity in the plunger, the plunger having a bottom end with an inner and an outer annular surface which encircle and are orthogonal to a longitudinal axis of the plunger and are separated a distance along that by a recess sidewall that encircles and faces the longitudinal axis to define a plunger recess in the bottom end of the plunger, the inner annular surface encircling and defining an opening to the recess which opening is in fluid communication with the fluid holding cavity of the plunger;
an annular cap having an annular cap bottom from which extend inner and outer sidewalls configured to fit over the bottom end of the plunger, the outer sidewall fitting over an outer surface of the bottom end of the plunger, the inner and outer sidewalls receiving the outer annular surface therebetween, the inner sidewall having an outer surface abutting the sidewall of the plunger recess, the inner surface of the inner sidewall defining a shaped cavity in fluid communication with the opening to the recess, the inner sidewall having a top end; and
a filter located the top end of the inner sidewall and the inner annular surface;
wherein a portion of the outer surface of the outer sidewall of the annular cap, at or by the bottom of the annular cap, extends outwardly a distance sufficient to form a first sealing surface that provides a fluid tight seal against a filter vial when the cap is inserted into the vial during use of the plunger assembly.

24. The tubular plunger assembly of claim 23, wherein the first sealing surface is formed by a flange on the end of the plunger which forces a portion of the cap's sidewall outward.

25. The tubular plunger assembly of claim 23, further comprising a frit or support interposed between the filter and the first annular surface.

26. The tubular plunger assembly of claim 23, further comprising a sealing surface facing along and encircling the longitudinal axis and formed on at least one of the first and second annular surfaces.

27. The tubular plunger assembly of claim 23, wherein the recess sidewall has a convexly curved shape and the outer surface of the inner sidewall of the cap has a mating concave shape.

28. The tubular plunger assembly of claim 23, wherein the shaped cavity is frustoconical.

29. The tubular plunger assembly of claim 23, wherein the tubular plunger has a sidewall that is thicker at the location of the second annular surface.

30. The tubular plunger assembly of claim 23, further comprising a removable closure configured to releasably form a fluid tight seal at the top end of the plunger.

31. The tubular plunger assembly of claim 23, wherein the plunger has a cross section orthogonal to the longitudinal axis that is one of a continuous curve or has at least three sides.

32. The tubular plunger assembly of claim 23, wherein the protrusion has a cross section orthogonal to the longitudinal axis that is one of a continuous curve or has at least three sides.

33. A filter vial kit, comprising:
the plunger assembly of claim 23; and
a filter vial having an open top and a closed bottom with a protrusion on the center of the bottom, the protrusion extending toward the top a distance about the same as a height of the inner sidewall of the annular cap measured along the longitudinal axis, the protrusion conforming in shape to the shaped cavity in the cap, the filter vial having an internal diameter slightly smaller than the outer diameter of at least a portion of the outer sidewall of the cap on the bottom of the plunger to form the fluid tight seal with the first sealing surface.

34. The filter vial kit of claim 33, wherein the filter vial has a removable cap and a volume of less than about 30 micro liters.

35. The filter vial kit of claim 33, wherein the interior bottom of the vial and protrusion are configured to conform to the exterior shape of the bottom of the cap and shaped recess.

36. The filter vial kit of claim 35, wherein the bottom of the filter vial has shallow channels formed therein which channels are in fluid communication with shallow channels in the surface of the protrusion, the channels orientated to carry fluid to the top of the protrusion during use.

37. The tubular plunger assembly of claim 33, wherein the plunger has a cross section orthogonal to the longitudinal axis that is one of a continuous curve or has at least three sides.

38. The tubular plunger assembly of claim 33, wherein the protrusion has a cross section orthogonal to the longitudinal axis that is one of a continuous curve or has at least three sides.

39. The filter vial kit of claim 33, wherein the vial has a constant inner diameter extending over a majority of a length of the vial from the closed bottom of the vial toward the top of the vial.

40. A filter vial kit, comprising:
a hollow tubular plunger having top and bottom ends with an opening at a bottom end of the plunger;
a filter extending across the opening in the bottom end of the plunger;
an annular cap fastened to the bottom end of the plunger, an outer sidewall of the cap extending along an outer surface of the bottom end of the plunger with a portion of that outer sidewall extending outward a predetermined distance to form a first sealing surface, the annular cap having an inner sidewall forming a shaped cavity in fluid communication with the opening in the bottom end of the plunger; and
a vial having an open top and a closed bottom having a central protrusion extending toward the open top of the vial, the vial having a sidewall that is sufficiently smaller in cross-section than the predetermined distance to form a fluid tight seal between the vial and annular cap, the bottom of the annular cap and the shaped recess being configured to mate with the shape of the a vial's bottom and the protrusion so as to force fluid in the vial through the shaped cavity and filter.

41. The filter vial kit of claim 40, wherein the vial, plunger and annular cap have cylindrical sidewalls.

42. The filter vial kit of claim 41, wherein the bottom of the vial has shallow channels in fluid communication with shallow channels in the surface of the protrusion so fluid is forced through the channels toward the filter as the annular cap fits snuggly against the vial's bottom and its protrusion.

43. The filter vial kit of claim 41, wherein the inner sidewall of the cap pushes the filter against a portion of the plunger to hold the filter in place.

44. The filter vial kit of claim 41, wherein the shaped cavity is frustoconical and the protrusion has a mating frustoconical shape with shallow channels in the surface of the protrusion to carry fluid to the top of the protrusion.

45. The filter vial kit of claim 41, wherein the plunger and vial have a cross section orthogonal to the longitudinal axis, which cross-section is one of a continuous curve or has at least three sides.

46. The tubular plunger assembly of claim 41, wherein the protrusion has a cross section orthogonal to the longitudinal axis which cross-section is one of a continuous curve or has at least three sides.

47. The filter vial kit of claim 40, wherein the vial has a constant inner diameter extending over a majority of a length of the vial from the closed bottom of the vial toward the top of the vial.

48. A filter vial, comprising:
   a plastic filter vial having an open top and a closed bottom connected by a cylindrical sidewall, the bottom having a protrusion extending a short distance along a longitudinal axis of the vial toward the top, the filter vial having a volume of about 30 microliters or less and a sidewall thickness of about 0.05 inches or less, wherein the bottom of the vial has shallow channels therein that are in fluid communication with shallow channels in an outer surface of the protrusion and orientated to carry fluid through the channels toward the top of the protrusion.

49. The filter vial of claim 48, wherein the protrusion is frustoconical and extends for a distance of less than about 0.2 inches.

50. The filter vial of claim 48, wherein the channels are radially orientated.

51. The filter vial of claim 48, wherein the vial has a constant inner diameter extending over a majority of a length of the vial from the closed bottom of the vial toward the top of the vial.

52. A filter vial and plunger assembly for filtering fluids, comprising:
   a tubular plunger having sidewalls defining an internal fluid cavity and having a top and bottom ends with a plunger opening in the bottom end of the plunger;
   an annular cap connected to the bottom end of the plunger, the annular cap having concentric inner and outer sidewalls with the outer sidewall connected to an outer sidewall of the plunger and the inner sidewall defining a shaped cavity in fluid communication with the plunger opening, the cap's outer sidewall having an outwardly extending first sealing surface at or by its bottom;
   a filter interposed between the cap's inner sidewall and the plunger opening;
   a vial having an open top and closed bottom joined by cylindrical sidewalls of sufficient diameter to form a fluid tight seal with the first sealing surface, the vial having a protrusion extending from the center of its bottom toward the top, the bottom of the annular cap and the bottom of the vial having complementary shapes, including complementary shapes of the protrusion and shaped cavity, to direct fluid from the vial through the shaped cavity during use.

53. The filter vial of claim 52, further comprising shallow channels in the bottom of the vial and in an exterior surface of the protrusion, the channels orientated to carry fluid toward the top of the protrusion.

54. The filter vial of claim 53, wherein the protrusion is frustoconical and the channels are radial.

55. The filter and plunger of claim 52, wherein the vial has a constant diameter extending over a majority of a length of the vial from the closed bottom of the vial toward the top of the vial.

* * * * *